(12) United States Patent
Backhaus et al.

(10) Patent No.: US 6,369,111 B1
(45) Date of Patent: Apr. 9, 2002

(54) SUBSTITUTED OXIMES

(75) Inventors: Dirk Backhaus, Köln; Herbert Gayer, Monheim; Stefan Hillebrand, Neuss; Peter Gerdes, Aachen; Martin Vaupel; Astrid Mauler-Machnik, both of Leichlingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/857,003

(22) PCT Filed: Nov. 22, 1999

(86) PCT No.: PCT/EP99/08976

§ 371 Date: May 30, 2001

§ 102(e) Date: May 30, 2001

(87) PCT Pub. No.: WO00/32563

PCT Pub. Date: Jun. 8, 2000

(30) Foreign Application Priority Data

Dec. 3, 1998 (DE) .......................... 198 55 810

(51) Int. Cl.$^7$ ..................... C07C 251/60; C07C 251/80; A01N 37/18; A01N 37/36

(52) U.S. Cl. ........................... 514/620; 560/35; 560/42; 564/147; 564/182; 514/538; 514/615

(58) Field of Search ..................... 560/35, 42; 564/147, 564/182; 514/538, 615, 620

(56) References Cited

FOREIGN PATENT DOCUMENTS

| | | |
|---|---|---|
| DE | 195 42 629 | 5/1997 |
| EP | 0 525 516 | 2/1993 |
| WO | 99/55665 | 11/1999 |

OTHER PUBLICATIONS

Tetrahedron Letters, (month unavailable) 1993, pp. 5151–5154, Bruce J. Martin, John M. Clough, Gerald Pattenden and Ian R. Waldron, Total Synthesis of the β–Methoxyacrylate–based Fungicide Myxothiazol.

*Primary Examiner*—Zinna Northington Davis
(74) *Attorney, Agent, or Firm*—Joseph C. Gil

(57) ABSTRACT

The invention relates to novel substituted oximes, to a process for their preparation and to their use as fungicides.

16 Claims, No Drawings

SUBSTITUTED OXIMES

FIELD OF THE INVENTION

The invention relates to novel substituted oximes, to a process for their preparation and to their use as fungicides.

BACKGROUND OF THE INVENTION

It is already known that certain compounds of a similar constitution to those described below have fungicidal properties (compare, for example, EP-A 525516). However, the fungicidal action of these compounds is, in particular at low application rates, not entirely satisfactory.

SUMMARY OF THE INVENTION

Substituted oximes according to the invention have microbicidal activity.

DETAILED DESCRIPTION

This invention, accordingly, provides the novel substituted oximes of the general formula (I),

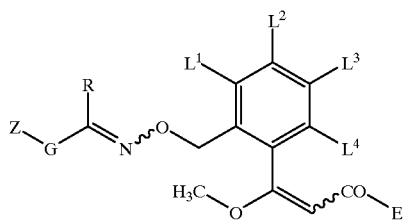

(I)

in which
E represents methoxy, ethoxy, amino or methylamino,
G represents a grouping

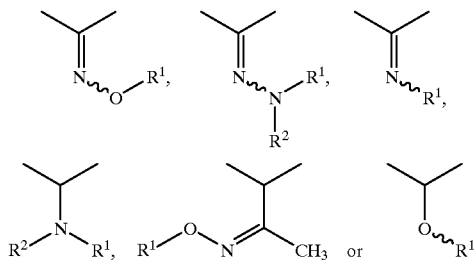

in which
R$^1$ and R$^2$ are identical or different and independently of one another each represents optionally substituted alkyl, alkenyl, alkinyl, aryl, cycloalkyl, alkylcarbonyl or arylcarbonyl, or
R$^1$ and R$^2$ together with the nitrogen atom to which they are attached form a saturated or unsaturated heterocyclic ring, and
Z represents cyano, alkoxycarbonyl, alkoxy, alkylthio, alkylsulfonyl, cycloalkoxy or in each case optionally substituted alkyl, cycloalkyl, cycloalkylalkyl, aryl, arylalkyl, heterocyclyl or heterocyclylalkyl,
R represents hydrogen, alkyl or in each case optionally substituted cycloalkyl or aryl, and
L$^1$, L$^2$, L$^3$ and L$^4$ are identical or different and independently of one another each represents hydrogen, halogen, cyano, nitro, in each case optionally halogen-substituted alkyl, alkoxy, alkylthio, alkylsulfinyl or alkylsulfonyl.

In the definitions, the saturated or unsaturated hydrocarbon chains, such as alkyl, are in each case straight-chain or branched, including in combination with heteroatoms, such as in alkoxy or alkylthio.

Halogenoalkyl is partially or fully halogenated alkyl. In the case of polyhalogenated halogenoalkyl, the halogen atoms can be identical or different. Preferred halogen atoms are fluorine and chlorine and in particular fluorine. If the halogenoalkyl carries further substituents, the maximum possible number of halogen atoms is reduced to the remaining free valencies.

Halogen generally represents fluorine, chlorine, bromine or iodine, preferably fluorine, chlorine or bromine, in particular fluorine or chlorine.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen and sulfur. If the ring contains a plurality of oxygen atoms, these are not adjacent. If appropriate, the cyclic compounds form, together with other carbocyclic or heterocyclic, fused-on or bridged rings, a polycyclic ring system. A polycyclic ring system can be attached via the heterocyclic ring or a fused-on carbocyclic ring. Preference is given to mono- or bicyclic ring systems, in particular to mono- or bicyclic aromatic ring systems.

Benzoheterocyclyl, as a sub-group of heterocyclyl, represents heterocyclyl to which a phenyl ring is fused.

Dibenzoheterocyclyl represents heterocyclyl to which two phenyl rings are fused.

Furthermore, it has been found that the novel substituted oximes of the general formula (I) are obtained when oximes of the formula (II)

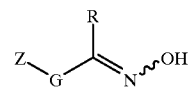

(II)

in which
G, R and Z are as defined above,
are reacted with a halogen compound of the general formula (III)

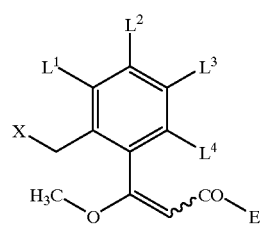

(III)

in which
E, L$^1$, L$^2$, L$^3$ and L$^4$ are as defined above and
X represents halogen,
if appropriate in the presence of a diluent and if appropriate in the presence of a catalyst.

Compounds of the formula (I) in which E represents amino or methylamino can also be obtained in a simple manner from compounds of the formula (I) in which E represents methoxy or ethoxy, by reaction with ammonia and methylamine, respectively, if appropriate in the presence of a diluent (compare also Tetrahedron Letters 1993, 5151–5154).

Compounds of the formula (I) in which R represents alkylsulfonyl can also be obtained in a simple manner from compounds of the formula (I) in which R represents alkylthio, by generally known oxidation methods.

Compounds of the formula (I) in which R represents alkoxy can also be obtained in a simple manner from compounds of the formula (I) in which R represents alkylsulfonyl, by generally known substitution reaction with alcohols.

Finally, it has been found that the novel substituted oximes of the general formula (I) have highly potent fungicidal action.

If appropriate, the compounds according to the invention can be present as mixtures of different possible isomeric forms, in particular of stereoisomers, such as, for example, E and Z or optical isomers. What is claimed are both the E and the Z isomers, the individual enantiomers, the racemates, and any mixtures of these isomers.

Preference is given to substituted oximes of the formula (I) in which

E represents methoxy, ethoxy, amino or methylamino,

G represents a grouping

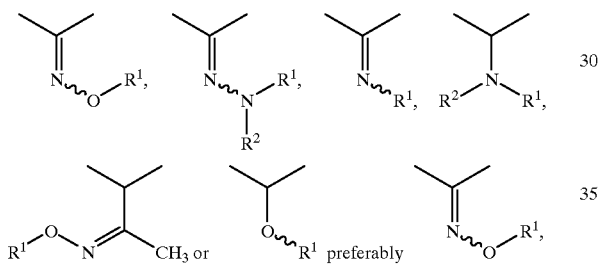

in which $R^1$ and $R^2$ are identical or different and independently of one another each represents alkyl or alkylcarbonyl having 1 to 6 carbon atoms, alkenyl having 2 to 6 carbon atoms or alkinyl having 2 to 6 carbon atoms, each of which is optionally substituted by halogen or alkoxy having 1 to 4 carbon atoms, or represents cycloalkyl having 3 to 8 carbon atoms, which is optionally substituted by halogen, alkyl or alkoxy having in each case 1 to 4 carbon atoms, or represents phenyl, phenylalkyl or heterocyclylalkyl having 1 to 4 carbon atoms in the alkyl moiety or phenylcarbonyl, each of which is optionally substituted in the phenyl moiety or heterocyclyl moiety, the substituents being selected from the list below:
halogen, cyano, nitro, alkyl, alkoxy, alkylthio, alkylsulfinyl or alkylsulfonyl having in each case 1 to 6 carbon atoms, halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms, in each case halogenoalkenyl or halogenoalkenyloxy having in each case 2 to 6 carbon atoms and 1 to 11 identical or different halogen atoms, or $R^1$ and $R^2$ together with the nitrogen atom to which they are attached form a saturated or unsaturated heterocyclic ring having 5 or 6 ring members, R represents alkyl having 1 to 4 carbon atoms or represents cycloalkyl having 3 to 6 carbon atoms or phenyl, each of which is optionally mono- to tetrasubstituted by halogen or alkyl, preferably represents methyl or cyclopropyl, in particular methyl, Z represents cyano, alkoxycarbonyl, alkoxy, alkylthio or alkylsulfonyl having in each case 1 to 4 carbon atoms in the alkyl moiety, cycloalkoxy having 5 or 6 carbon atoms or represents alkyl or halogenoalkyl having in each case 1 to 4 carbon atoms and being in each case optionally monosubstituted by cyano or alkoxy, or represents cycloalkyl or cycloalkylalkyl having in each case 3 to 7 carbon atoms in the cycloalkyl moiety and 1 to 4 carbon atoms in the alkyl moiety, each of which is optionally mono- to tetrasubstituted by halogen or alkyl; or represents heterocyclyl, benzoheterocyclyl, dibenzoheterocyclyl or heterocyclylalkyl having in each case 3 to 7 ring members in the heterocyclyl moiety and 1 to 4 carbon atoms in the alkyl moiety and being optionally substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 9 halogen atoms or phenyl;

or represents aryl or arylalkyl having in each case 6 to 10 carbon atoms in the aryl moiety and 1 to 4 carbon atoms in the alkyl moiety and being in each case optionally mono- to tetrasubstituted in the aryl moiety by identical or different substituents, the possible substituents preferably being selected from the list below:

halogen, cyano, nitro, amino, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulfinyl or alkylsulfonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, methyl, trifluoromethyl and ethyl;

phenoxy or phenylalkoxy having 1 to 4 carbon atoms in the alkyl moiety, each of which is optionally substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 9 halogen atoms, heterocyclyl, heterocyclyloxy, heterocyclylthio, heterocyclylsulfinyl or heterocyclylsulfonyl having 5 or 6 ring members and being in each case optionally substituted by halogen, alkyl, alkoxy, alkylthio, alkylsulfinyl or alkylsulfonyl having 1 to 4 carbon atoms, halogenoalkoxy, halogenoalkylthio, halogenoalkylsulfmyl or halogenoalkylsulfonyl having 1 to 4 carbon atoms and 1 to 9 halogen atoms or phenyl, or a grouping

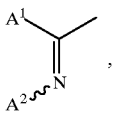

in which
A$^1$ represents hydrogen or alkyl having 1 to 4 carbon atoms or cycloalkyl having 3 to 6 carbon atoms and
A$^2$ represents hydroxyl, amino, methylamino, methyl, phenyl, benzyl, alkoxy, alkylamino, dialkylamino having 1 to 4 carbon atoms in the respective alkyl chains and
L$^1$, L$^2$, L$^3$ and L$^4$ are identical or different and independently of one another each represents hydrogen, halogen, cyano, nitro, represents alkyl, alkoxy, alkylthio, alkylsulfinyl or alkylsulfonyl having in each case 1 to 6 carbon atoms and being in each case optionally substituted by 1 to 5 halogen atoms, preferably represents hydrogen or methyl and in particular hydrogen.

Particular preference is given to substituted oximes of the formula (I), in which
E represents methoxy, ethoxy, amino or methylamino,
G represents a grouping

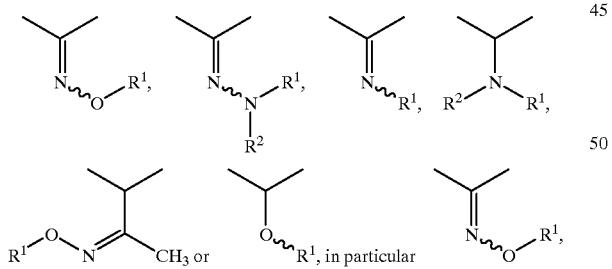

in which
R$^1$ and R$^2$ are identical or different and independently of one another represent in each case optionally fluorine-, chlorine- or methoxy-substituted methyl, ethyl, n- or i-propyl, n-, i-, s- or t-butyl, acetyl, propionyl, allyl, crotonyl, propargyl or represent optionally fluorine-, chlorine-, methyl- or methoxy-substituted cyclopentyl or cyclohexyl or represent phenyl, benzyl or benzoyl, each of which is optionally substituted in the phenyl moiety, the substituents being selected from the list below:

fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulfinyl or trifluoromethylsulfonyl, R$^1$ and R$^2$ together with the nitrogen atom to which they are attached form a pyrrole, pyrrolidine, imidazole or triazole ring, R represents methyl, ethyl, n- or i-propyl, or represents cyclopropyl, cyclobutyl, cyclopentyl or phenyl, each of which is optionally mono- to tetrasubstituted by fluorine, chlorine, methyl or ethyl, Z represents cyano, methoxycarbonyl, ethoxycarbonyl, methyl, ethyl, n- or i-propyl, n-, i-, s- or t-butyl, trifluoromethyl, trifluoroethyl, methoxy, ethoxy, n- or i-propoxy, methylthio, ethylthio, methylsulfonyl, ethylsulfonyl, cyclopentyloxy or cyclohexyloxy or represents cyclopentyl or cyclohexyl, each of which is optionally mono- to tetrasubstituted by fluorine, chlorine, methyl or ethyl; or represents optionally methyl-, ethyl-, fluorine-, chlorine-, bromine-, trifluoromethyl-, phenyl-substituted thienyl, pyridyl, frryl, piperazinyl, thiazolyl, dioxazinyl, benzimidazolyl, benzothiazolyl, benzofuranyl, benzopyrazolyl, dibenzothiazinyl, thienylmethyl, pyridylmethyl or furylmethyl;

or represents benzyl 1-phenylethyl or 2-phenylethyl, each of which is optionally mono- to tetrasubstituted by identical or different substituents, represents in particular substituted phenyl, the possible substituents preferably being selected from the list below:

fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulfinyl, ethylsulfinyl, methylsulfonyl or ethylsulfonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulfinyl or trifluoromethylsulfonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case doubly attached propanediyl, ethyleneoxy, methylenedioxy, ethylenedioxy, each of which is optionally mono- to tetrasubstituted by identical or different substituents from the group consisting of fluorine, chlorine, methyl and trifluoromethyl in each case optionally fluorine-, chlorine-, methyl-, trifluoromethyl- or methoxy-substituted phenoxy or benzyl,
heterocyclyl, heterocyclyloxy, heterocyclylthio, heterocyclylsulfinyl or heterocyclylsulfonyl having 5 or 6 ring members and being in each case optionally substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 9 halogen atoms or phenyl,
represents optionally methyl-, ethyl-, fluorine-, chlorine-, bromine-, trifluoromethyl-, phenyl-substituted thienyl, imidazolyl, thiadiazolyl, pyridyl, furyl, piperazinyl, thiazolyl, dioxazinyl, thiadiazolylsulfonyl;
or a grouping

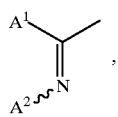

where
A¹ represents hydrogen or methyl and
A² represents hydroxyl, methoxy, ethoxy, amino, methylamino, methyl, phenyl or benzyl, and
$L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroetioxy, difluoromethylthio, difluorochloromethylthio, trifluoromethylthio, trifluoromethylsulfinyl or trifluoromethylsulfonyl, preferably represents hydrogen or [lacuna] and in particular hydrogen.

Independently of the abovementioned definitions, $R^1$ and $R^2$ in particular represent methyl, ethyl, n- or i-propyl, benzyl or 6-chloropyridin-3-ylmethyl, preferably methyl.

Preference is given to compounds in which $L^1$, $L^2$, $L^3$ and $L^4$ represent hydrogen.

Preference is given to compounds in which E represent amino, methylamino or, in particular, methoxy.

Preference is given to compounds in which R represents methyl.

Preference is given to compounds in which G represents

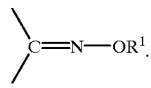

The abovementioned general or preferred radical definitions apply both to the end products of the formula (I) and, correspondingly, to the starting materials or intermediates required in each case for the preparation.

These radical definitions can be combined with one another as desired, i.e. including combinations between the given ranges of preferred compounds.

The formula (II) provides a general definition of the oximes required as starting materials for carrying out the process according to the invention. In this formula (II), G, R and Z preferably or in particular have those meanings which have already been mentioned, in connection with the description of the compounds of the formula (I) according to the invention, as being preferred or as being particularly preferred for G, R and Z.

The oximes of the formula (II) are known or can be prepared by known methods (compare, for example, WO 96-32373 and WO 97-06133).

The formula (III) provides a general definition of the halogen compounds further required as starting materials for carrying out the process according to the invention. In this formula (III), E, $L^1$, $L^2$, $L^3$ and $L^4$ preferably or in particular have those meanings which have already been mentioned in connection with the description of the compounds of the formula (I) according to the invention as being preferred or as being particularly preferred for E, $L^1$, $L^2$, $L^3$ and $L^4$. X represents halogen, preferably chlorine or bromine.

The halogen compounds of the formula (III) are known and can be prepared by known methods (compare EP-A 525516).

Suitable diluents for carrying out the process according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; sulfoxides, such as dimethyl sulfoxide; or sulfones, such as sulfolane.

The process according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, carbonates or bicarbonates, such as, for example, sodium hydride, sodium amide, sodium methoxide, sodium ethoxide, potassium tert-butoxide, sodium hydroxide, potassium hydroxide, sodium carbonate, potassium carbonate, potassium bicarbonate or sodium bicarbonate, and also tertiary amines, such as trimethylamine, triethylamine, tributylamine, N,N-dimethylaniline, N,N-dimethylbenzylamine, pyridine, N-methylpiperidine, N-methylmoipholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures from 20° C. to 180° C., preferably at temperatures from 20° C. to 150° C.

For carrying out the process according to the invention for preparing the compounds of the formula (a), in general from 0.5 to 2 mol, preferably from 0.8 to 1.5 mol. of halogen compound of the formula (III) are employed per mole of oxime of the formula (II).

The process according to the invention is generally carried out under atmospheric pressure. However, it is also possible to operate under elevated or reduced pressure—in general between 0.1 bar and 10 bar.

The practice of the reaction and the work-up and isolation of the reaction products are carried out by generally customary processes (compare also the Preparation Examples).

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea (conidia form: Drechslera, syn: Helminthosporium);*

Cochliobolus species, such as, for example, *Cochliobolus sativus (conidia form: Drechslera, syn: Helminthosporium);*

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases such as, for example, against Erysiphe species and Leptosphaeria species.

The active compounds according to the invention are also suitable for increasing the harvest yield. Moreover, they have reduced toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes) and against slime organisms and algae.

Microorganisms of the following genera may be mentioned as examples:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa,*

Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example ligno-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecitgins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:
aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyfithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminum, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulfate, copper oxide, oxine-copper and Bordeaux mixture, mancopper, mancozeb, maneb, meferimzone, mepanipyrim, mepronil, metalaxyl, metconazole, methasulfocarb, methfuroxamn, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulfur and sulfur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-b-propyl-1H-1,2,4-triazole-1-ethanol,
α-(2,4-dichlorophenyl)-β-methoxy-a-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-a-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulfonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulfonyl]-5-(trichloromethyl)-1,3,4-thiadiazole,
2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulfate,
9H-xanthene-9-carboxylic-[(phenylamino)-carbonyl] hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium hydrogencarbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetaride,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
  bromopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.
Insecticides/Acaricides/Nematicides:
  abamectin, acephate, acetamiprid, acrinathrin, alanycarb, aldicarb, aldoxycarb, alpha-cypermethrin, alphamethrin, amitraz, avernectin, AZ 60541, azadirachtin, aza-methiphos, azinphos A, azinphos M, azocyclotin,
  *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, efusilanate, emamectin, empenthrin, endosulfan, Entomopfthora spp., esfenvalerate, ethiofencarb, ethion, ethoprophos, etofqnprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, filrathiocarb, granulosis viruses halofenozide, HCH, heptenophos, hexaflumuron, hexythiazox, hydroprene, imidacloprid, isazofos, isofenphos, isoxathion, ivermectin, nuclear polyhedrosis viruses lambda-cyhalothrin, lufenuron malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron omethoate, oxamyl, oxydemethon M

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*

YI 5302 zeta-cypermethrin, zolaprofos (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine 2-(2-chloro-6-fluorophenyl)-4-[4-(1,1-dimethylethyl) phenyl]-4,5-dihydro-oxazole, 2-(acetlyoxy)-3-dodecyl-1,4-naphthalenedione 2-chloro-N-[[[4-(1-phenylethoxy)-phenyl]-amino]-carbonyl]-benzamide 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348, 2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides, or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compounds are generally between 0.1 and 10,000 g/ha, preferably between 10 and 1000 g/ha. In the treatment of seed, the application rates of active compounds are generally between 0.001 and 50 g per kilogram of seed, preferably between 0.01 and 10 g per kilogram of seed. In the treatment of the soil, the application rates of active compound are generally between 0.1 and 10, 000 g/ha, preferably between 1 and 5000 g/ha.

The compositions used for protecting industrial materials comprise the active compounds generally in an amount of from 1 to 95%, preferably from 10 to 75%.

The use concentrations of the active compounds according to the invention depend on the species and the occurrence of the microorganisms to be controlled, and on the composition of the material to be protected. The optimum rate of application can be determined by test series. The use concentrations are generally in the range from 0.001 to 5% by weight, preferably from 0.05 to 1.0% by weight, based on the material to be protected.

The activity and the activity spectrum of the active compounds to be used according to the invention in the protection of materials, or the compositions, concentrates or quite generally formulations preparable therefrom, can be increased by adding, if appropriate, other antimicrobially active compounds, fungicides, bactericides, herbicides, insecticides or other active compounds for broadening the activity spectrum or obtaining particular effects, such as, for example, the additional protection against insects. These mixtures may have a broader activity spectrum than the compounds according to the invention.

PREPARATION EXAMPLES

Example (1)

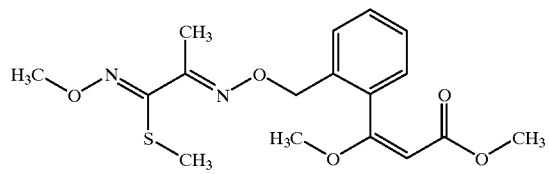

A solution of 1.63 g (10 mMol) of methyl 2-hydroxyamino-N-methoxy-thiopropionimidate in 80 ml of dimethylformamide is cooled to 0° C., admixed with 333 mg (10 mMol) of sodium hydride (75% strength) and stirred without further cooling for 2 hours. 2.85 g (10 mMol) of methyl 3-(2-bromomethyl-phenyl)-3-methoxy-acrylate are then added, and the mixture is stirred at 20° C. for 18 hours. The reaction mixture is poured into water and extracted twice with ethyl acetate. The combined organic phases are washed with saturated sodium chloride solution, dried over sodium sulfate and concentrated under reduced pressure. The residue is chromatographed over silica gel using cyclohexane/ethyl acetate (4:1).

This gives 3.07 g (84% of theory) of methyl 3-methoxy-3-[2-(2-methoxyamino-1-methyl-2-methylthio-ethylideneaminooxymethyl)-phenyl]-acrylate.

HPLC: logP=3.5

Example (2)

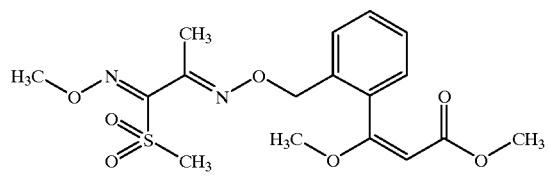

340 mg (0.93 mMol) of methyl 3-methoxy-3-[2-(2-methoxyimino-1-methyl-2-methylthioethylideneaminooxymethyl)-phenyl]-acrylate are dissolved in a mixture of 2 ml of carbon tetrachloride, 2 ml of acetonitrile and 4 ml of water, and the mixture is cooled to 10° C. 640 mg (3.0 mMol) of sodium periodate and 1 mg (0.005 mMol) of ruthenium-III chloride hydrate are added, and the mixture is stirred at 20° C. for 3 hours. The reaction mixture is poured into water and extracted three times with ethyl acetate. The combined organic phases are washed with sodium chloride solution, dried over sodium sulfate and concentrated under reduced pressure. The residue is chromatographed over silica gel using cyclohexane/ethyl acetate (1:1). This gives 320 mg (86% of theory) of methyl 3-[2-(2-methanesulfonyl-2-methoxyimino-1-methyl-ethylideneaminooxymethyl)-phenyl]-3-methoxy-acrylate.

HPLC: logP=2.79

Example (3)

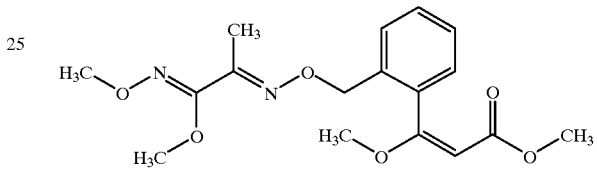

0.21 ml (1.0 mMol) of a 30% strength sodium methoxide solution in methanol are added to a solution of 200 mg (0.5 mMol) of methyl 3-[2-(2-methanesulfonyl-2-methoxyimino-1-methyl-ethylideneaminooxymethyl)-phenyl]-3-methoxy-acrylate in 10 ml of tetrahydrofuran, and the mixture is stirred at 20° C. for 4 hours. The reaction mixture is poured into a saturated ammonium chloride solution and extracted three times with ethyl acetate. The combined organic phases are dried over sodium sulfate and concentrated under reduced pressure. The residue is chromatographed over silica gel using cyclohexane/ethyl acetate (1:1).

This gives 160 mg (91% of theory) of methyl 3-methoxy-3-[2-(2-methoxy-2-methoxyimino-1-methyl-ethylideneaminooxymethyl)-phenyl]-acrylate.

HPLC: logP=3.05

Analogously to Examples (1–3), and in accordance with the general description of the preparation process according to the invention, it is also possible to obtain the compounds of the formula (I-a) according to the invention listed in Table 1 below:

(I-a)

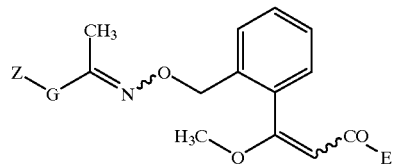

TABLE 1
| Ex. No. | G | Z | E | Phys. data |
|---|---|---|---|---|
| 4 | 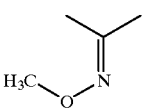 | phenyl | —OCH$_3$ | logP(s): 4.2 |
| 5 | 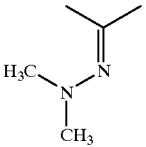 | —CH$_3$ | —OCH$_3$ | |
| 6 | 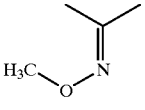 | —CH$_3$ | —OCH$_3$ | logP(n): 3.9 |
| 7 | 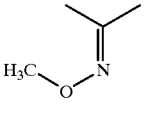 | -i-C$_3$H$_7$ | —OCH$_3$ | logP(n): 4.6 |
| 8 | 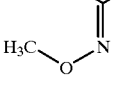 | —COOCH$_3$ | —OCH$_3$ | logP(s): 3.3 |
| 9 | 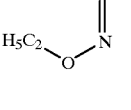 | -i-C$_3$H$_7$ | —OCH$_3$ | logP(s): 5.2 |
| 10 | 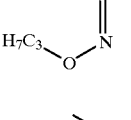 | -i-C$_3$H$_7$ | —OCH$_3$ | logP(s): 5.6 |
| 11 | 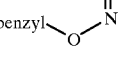 | -i-C$_3$H$_7$ | —OCH$_3$ | logP(s): 5.52 |
| 12 | 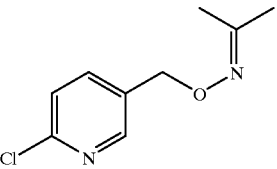 | -i-C$_3$H$_7$ | —OCH$_3$ | log(s): 5.23 |
| 13 | 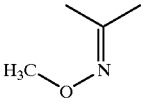 | -O-i-C$_3$H$_7$ | —OCH$_3$ | logP(s): 3.73 |
| 14 | 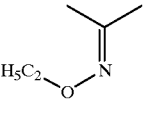 | -i-C$_3$H$_7$ | —NHCH$_3$ | logP(s): 3.91 |

TABLE 1-continued

| Ex. No. | G | Z | E | Phys. data |
|---|---|---|---|---|
| 15 | H5C2—O—N=C(CH3)— | -i-C3H7 | —NH2 | logP(s): 3.57 |
| 16 | H3C—O—N=C(CH3)— | —OC2H5 | —OCH3 | logP(s): 3.40 |
| 17 | H3C—O—N=C(CH3)— | —OC2H5 | —OC2H5 | logP(s): 3.75 |

The $^1$H-NMR spectra were recorded in deuterochloroform (CDCl$_3$) or hexa-deuterodimethyl sulfoxide (DMSO-d$_6$) using tetramethylsilane (TMS) as internal standard. What is stated is the chemical shift as δ value in ppm.

The logP values were determined in accordance with EEC Directive 79/831 Annex V. A8 by HPLC (gradient method, acetonitrile/0.1% aqueous phosphoric acid (s) or gradient method, acetonitrile/0.1% water (n))

USE EXAMPLES

Example A

*Leptosphaeria nodorum* test (wheat)/protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of 80%.

Evaluation is carried out 10 days after the inoculation. 0% means an efficacy which corresponds to that of the control, whereas an efficacy of 100% means that no infection is observed.

In this test, the compound according to the invention listed in Example (4) exhibits, at an application rate of 250 g/ha, an efficacy of 90% or more.

Example B

Erysiphe test (barley)/protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis* f.sp. *hordei*.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

In this test, the compound according to the invention listed in Example (4) exhibits, at an application rate of 250 g/ha, an efficacy of 90% or more.

Example C

Erysiphe test (wheat)/protective

Solvent: 25 parts by weight of N,N-dimethylacetarnide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

In this test, the compounds according to the invention listed in Examples (6) and (7) exhibit, at an application rate of 250 g/ha, an efficacy of 100%.

Example D

Erysiphe test (wheat)/curative

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. *tritici*. 48 hours after the inoculation, the plants are sprayed with the preparation of active compound at the stated application rate.

The plants are placed in a greenhouse at a temperature of 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

In this test, the substances according to the invention listed in Examples (6) and (7) exhibit, at an application rate of 250 g/ha, an efficacy of 100%.

Example E
Puccinia test (wheat)/protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of about 80% to promote the development of mildew pustules.

Evaluation is carried out 10 days after the inoculation. 0% means an efficacy which corresponds to that of the control, whereas an efficacy of 100% means that no infection is observed.

In this test, the compound according to the invention listed in Example (7) exhibits, at an application rate of 250 g/ha, an efficacy of 100%.

Example F
Erysiphe test (barley)/curative

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are dusted with spores of *Erysiphe graminis* f.sp. *hordei*. 48 hours after the inoculation, the plants are sprayed with the preparation of active compound at the stated application rate.

The plants are placed in a greenhouse at a temperature of about 20° C. and a relative atmospheric humidity of about 80% to promote the development of mildew pustules.

Evaluation is carried out 10 days after the inoculation. 0% means an efficacy which corresponds to that of the control, whereas an efficacy of 100% means that no infection is observed.

In this test, the compound according to the invention listed in Example (7) exhibits, at an application rate of 250 g/ha, an efficacy of 100%.

Example G
Plasmopara test (grapevine)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the compound according to the invention listed in Example (4) exhibits, at an application rate of 100 g/ha, an efficacy of 90% or more.

Example H
Venturia test (apple)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 12 days after the inoculation. 0% means an efficacy which corresponds to that of the control, whereas an efficacy of 100% means that no infection is observed.

In this test, the compound according to the invention listed in Example (4) exhibits, at an application rate of 10 g/ha, an efficacy of 100%.

Example I
Pyricularia test (rice)/protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound at the stated application rate. After the spray coating has dried on, the plants are inoculated with an aqueous spore suspension of *Pyricularis oryzae* and then remain at 100% rel. atmospheric humidity and 26° C. for 24 h. The plants are then placed in a greenhouse at 80% rel. atmospheric humidity and 26° C.

Evaluation is carried out 7 days after the inoculation. 0% means an efficacy which corresponds to that of the control, whereas an efficacy of 100% means that no infection is observed.

In this test, the compound according to the invention listed in Example (7) exhibits, at an application rate of 125 g/ha, an efficacy of 97% or more.

What is claimed is:

1. A compound of the formula (I),

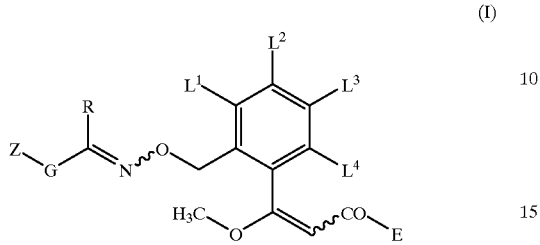

(I)

wherein

E represents methoxy, ethoxy, amino or methylamino,

G represents a grouping

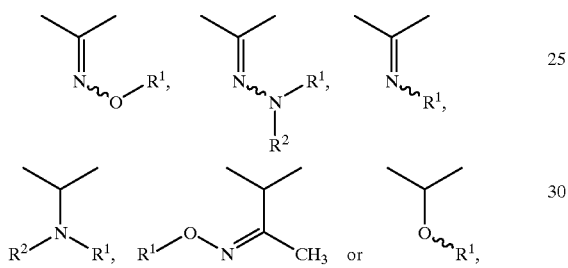

wherein $R^1$ and $R^2$ are identical or different and independently of one another each represents unsubstituted or substituted alkyl, alkenyl, alkinyl, aryl, cycloalkyl, alkylcarbonyl or arylcarbonyl, or $R^1$ and $R^2$ together with the nitrogen atom to which they are attached form a saturated or unsaturated heterocyclic ring, and Z represents cyano, alkoxycarbonyl, alkoxy, alkylthio, alkylsulfonyl, cycloalkoxy or in each case unsubstituted or substituted alkyl, cycloalkyl, cycloalkylalkyl, aryl, arylalkyl, heterocyclyl or heterocyclylalkyl, R represents hydrogen, alkyl or in each case unsubstituted or substituted cycloalkyl or aryl, and $L^1$, $L^2$, $L^3$ and $L^4$ are identical or different and independently of one another each represents hydrogen, halogen, cyano, nitro, in each case unsubstituted or halogen-substituted alkyl, alkoxy, alkylthio, alkylsulfinyl or alkylsulfonyl.

2. A compound according to claim 1, wherein

E represents methoxy, ethoxy, amino or methylamino,

G represents a grouping

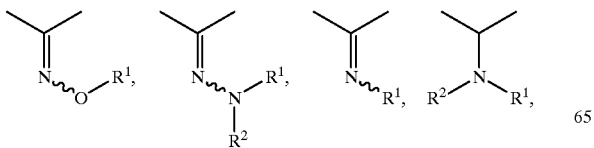

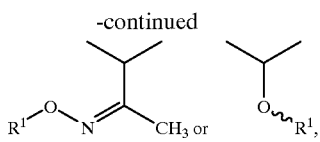

wherein $R^1$ and $R^2$ are identical or different and independently of one another each represents alkyl or alkylcarbonyl having 1 to 6 carbon atoms, alkenyl having 2 to 6 carbon atoms or alkinyl having 2 to 6 carbon atoms, each of which is unsubstituted or substituted by halogen or alkoxy having 1 to 4 carbon atoms, or represents cycloalkyl having 3 to 8 carbon atoms, which is unsubstituted or substituted by halogen, alkyl or alkoxy having in each case 1 to 4 carbon atoms, or represents phenyl, phenylalkyl or heterocyclylalkyl having 1 to 4 carbon atoms in the alkyl moiety or phenylcarbonyl, each of which is unsubstituted or substituted in the phenyl moiety or heterocyclyl moiety, the substituents being selected from the list below:

halogen, cyano, nitro, alkyl, alkoxy, alkylthio, alkylsulfinyl or alkylsulfonyl having in each case 1 to 6 carbon atoms, halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms, in each case halogenoalkenyl or halogenoalkenyloxy having in each case 2 to 6 carbon atoms and 1 to 11 identical or different halogen atoms, or $R^1$ and $R^2$ together with the nitrogen atom to which they are attached form a saturated or unsaturated heterocyclic ring having 5 or 6 ring members, R represents alkyl having 1 to 4 carbon atoms or represents cycloalkyl having 3 to 6 carbon atoms or phenyl, each of which is unsubstituted or mono- to tetrasubstituted by halogen or alkyl, Z represents cyano, alkoxycarbonyl, alkoxy, alkylthio or alkylsulfonyl having in each case 1 to 4 carbon atoms in the alkyl moiety, cycloalkoxy having 5 or 6 carbon atoms;

or represents alkyl or halogenoalkyl having in each case 1 to 4 carbon atoms and being in each case unsubstituted or monosubstituted by cyano or alkoxy, or represents cycloalkyl or cycloalkylalkyl having in each case 3 to 7 carbon atoms in the cycloalkyl moiety and 1 to 4 carbon atoms in the alkyl moiety, each of which is unsubstituted or mono- to tetrasubstituted by halogen or alkyl;

or represents heterocyclyl, benzoheterocyclyl, dibenzoheterocyclyl or heterocyclylalkyl having in each case 3 to 7 ring members in the heterocyclyl moiety and 1 to 4 carbon atoms in the alkyl moiety and being unsubstituted or substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 9 halogen atoms or phenyl:

or represents aryl or arylalkyl having in each case 6 to 10 carbon atoms in the aryl moiety and 1 to 4 carbon atoms in the alkyl moiety and being in each case unsubstituted or mono- to tetrasubstituted in the aryl moiety by identical or different substituents, the possible substituents being selected from the list below:

halogen, cyano, nitro, amino, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulfinyl or alkylsulfonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is unsubstituted or mono- to tetrasubstituted by identical or different substituents from the group consisting of fluorine, chlorine, methyl trifluoromethyl and ethyl;

phenoxy or phenylalkoxy having 1 to 4 carbon atoms in the alkyl moiety, each of which is unsubstituted or- substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 9 halogen atoms, heterocyclyl, heterocyclyloxy, heterocyclylthio, heterocyclylsulfinyl or heterocyclylsulfonyl having 5 or 6 ring members and being in each case unsubstituted or substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 9 halogen atoms or phonyl, or a grouping

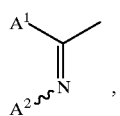

wherein $A^1$ represents hydrogen or alkyl having 1 to 4 carbon atoms or cycloalkyl having 3 to 6 carbon atoms and $A^2$ represents hydroxyl, amino, methylamino, methyl, phenyl, benzyl, alkoxy, alkylamino, dialkylamino having 1 to 4 carbon atoms in the respective alkyl chains and $L^1$, $L^2$, $L^3$ and $L^4$ are identical or different and independently of one another each represents hydrogen, halogen, cyano, nitro, or represents alkyl, alkoxy, alkylthio, alkylsulfinyl or alkylsulfonyl having in each case 1 to 6 carbon atoms and being in each case unsubstituted or substituted by 1 to 5 halogen atoms.

3. A compound according to claim 1, wherein

E represents methoxy, ethoxy, amino or methylamino,

G represents a grouping

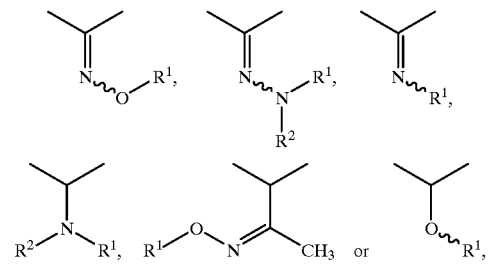

wherein $R^1$ and $R^2$ are identical or different and independently of one another represent in each case unsubstituted or fluorine-, chlorine- or methoxy-substituted methyl, ethyl, n- or i-propyl, n-, i-, s- or t-butyl, acetyl, propionyl, allyl, crotonyl, propargyl or represent unsubstituted or fluorine-, chlorine-, methyl- or methoxy-substituted cyclopentyl or cyclohexyl or represent phenyl, benzyl or benzoyl, each of which is unsubstituted or substituted in the phenyl moiety, the substituents being selected from the list below:

fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulfinyl or trifluoromethylsulfonyl, $R^1$ and $R^2$ together with the nitrogen atom to which they are attached form a pyrrole, pyrrolidine, imidazole or triazole ring, R represents methyl, ethyl, n- or i-propyl, or represents cyclopropyl, cyclobutyl, cyclopentyl or phenyl, each of which is unsubstituted or mono- to tetrasubstituted by fluorine, chlorine, methyl or ethyl, Z represents cyano, methoxycarbonyl, ethoxycarbonyl, methyl, ethyl, n-or i-propyl, n-, i-, s- or t-butyl, trifluoromethyl, trifluoroethyl, methoxy, ethoxy, n- or i-propoxy, methylthio, ethylthio, methylsulfonyl, ethylsulfonyl, cyclopentyloxy or cyclohexyloxy, or represents cyclopentyl or cyclohexyl, each of which is unsubstituted or mono- to tetrasubstituted by fluorine, chlorine, methyl or ethyl;

or represents unsubstituted or methyl-, ethyl-, fluorine-, chlorine-, bromine-, trifluoromethyl-, phenyl-substituted thienyl, pyridyl, furyl, piperazinyl, thiazolyl, dioxazinyl, benzimidazolyl, benzothiazolyl, benzofuranyl, benzopyrazolyl, dibenzothiazinyl, thienylmethyl, pyridylmethyl or furylmethyl;

or represents benzyl, 1-phenylethyl or 2-phenylethyl, each of which is unsubstituted or mono- to tetrasubstituted by identical or different substituents, or substituted phenyl, the possible substituents being selected from the list below:

fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulfinyl, ethylsulfinyl, methylsulfonyl or ethylsulfonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulfinyl or trifluoromethylsulfonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case doubly attached propanediyl, ethyleneoxy, methylenedioxy, ethylenedioxy, each of which is unsubstituted or mono- to tetrasubstituted by identical or different substituents from the group consisting of fluorine, chlorine, methyl and trifluoromethyl in each case unsubstituted or fluorine-, chlorine-, methyl-, trifluoromethyl- or methoxy-substituted phenomy or benzyl, heterocyclyl, heterocyclyloxy, heterocyclylthio, heterocyclylsulfinyl or heterocyclylsulfonyl having 5 or 6 ring members and being in each case unsubstituted or substituted by halogen, alkyl, alkoxy, alkylthio, alkylsulfinyl or alkylsulfonyl having 1 to 4 carbon atoms, halogenoalkoxy, halogenoalkylthio, halogenoalkylsulfinyl or halogenoalkylsulfonyl having 1 to 4 carbon atoms and 1 to 0 halogen atoms or phenyl, or represents unsubstituted methyl-, ethyl-, fluorine-, chlorine-, bromine-, trifluoromethyl-, phenyl-substituted thienyl, imidazolyl, thiadiazolyl, pyridyl, furyl, piperazinyl, thiazolyi, dioxazinyl, thiadiazolylsulfonyl;

or a grouping

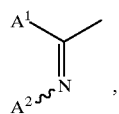

where $A^1$ represents hydrogen or methyl and $A^2$ represents hydroxyl, methoxy, ethoxy, amino, methylamino, methyl, phenyl or benzyl, and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulfinyl, ethylsulfinyl, methylsulfonyl or ethylsulfonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulfinyl or trifluoromethylsulfonyl.

4. A compound according to claim 1, wherein
$R^1$ and $R^2$ represent methyl, ethyl, n- or i-propyl, benzyl or 6-chloropyridin-3-ylmethyl.

5. A composition comprising a compound according the claim 1 and extenders and/or carriers.

6. A process for preparing compositions, comprising the step of mixing a compound according to claim 1 with extenders and/or carriers and/or surfactants.

7. A process for preparing a compound according to claim 1, comprising the step of reacting an oxime of the formula (II)

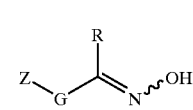

wherein

G, R and Z are as defined in claim 1 with a halogen compound of the formula (III)

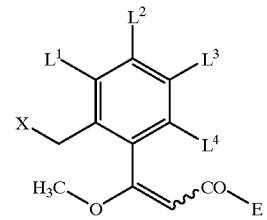

wherein

E, $L^1$, $L^2$, $L^3$ and $L^4$ are as defined in claim 1 and

X represents halogen.

8. A compound according to claim 2, wherein
G represents

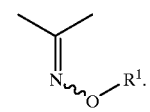

9. A compound according to claim 2, wherein $L^1$, $L^2$, $L^3$ and $L^4$ each independently represent hydrogen or methyl.

10. A compound according to claim 9, wherein $L^1$, $L^2$, $L^3$ and $L^4$ each represent hydrogen.

11. A compound according to claim 2, wherein R represents methyl or cylcopropyl.

12. A compound according to claim 11, wherein R represents methyl.

13. A compound according to claim 2, wherein E represents methoxy.

14. A compound according to claim 2, wherein E represents amino or methylamino.

15. A method of control microorganisms, comprising the step of applying a compound according to claim 1 to microorganisms and/or their habitat.

16. A method of control microorganisms, comprising the step of applying a composition according to claim 5 to microorganisms and/or their habitat.

* * * * *